United States Patent
Warner (10) Patent No.: US 11,653,138 B2
(45) Date of Patent: May 16, 2023

(54) ACOUSTIC REFLEX DETECTION

(71) Applicant: David Patrick Warner, Overland Park, KS (US)

(72) Inventor: David Patrick Warner, Overland Park, KS (US)

(*) Notice: Subject to any disclaimer, the term of this patent is extended or adjusted under 35 U.S.C. 154(b) by 0 days.

(21) Appl. No.: 17/523,491

(22) Filed: Nov. 10, 2021

(65) Prior Publication Data

US 2022/0248121 A1    Aug. 4, 2022

Related U.S. Application Data

(60) Provisional application No. 63/076,493, filed on Sep. 10, 2020.

(51) Int. Cl.
*H04R 1/10* (2006.01)
*H04R 29/00* (2006.01)
*A61B 5/12* (2006.01)

(52) U.S. Cl.
CPC ........... *H04R 1/1041* (2013.01); *A61B 5/126* (2013.01); *H04R 1/1016* (2013.01); *H04R 29/001* (2013.01); *H04R 2430/01* (2013.01)

(58) Field of Classification Search
CPC .. H04R 1/1041; H04R 1/1016; H04R 29/001; H04R 2430/01; A61B 5/126
See application file for complete search history.

(56) References Cited

U.S. PATENT DOCUMENTS

| | | | | |
|---|---|---|---|---|
| 2015/0304774 A1* | 10/2015 | Ambrose | ................. | H04R 1/10 381/74 |
| 2016/0127818 A1* | 5/2016 | Ambrose | ............. | H04R 1/1066 381/380 |
| 2018/0063618 A1* | 3/2018 | Boesen | ................ | H04R 1/1041 |
| 2019/0038188 A1* | 2/2019 | Lodwig | ................ | A61B 5/7214 |
| 2021/0236339 A1* | 8/2021 | Bonnet | .................. | H04R 29/00 |
| 2022/0361787 A1* | 11/2022 | Burwinkel | ............. | A61B 5/1114 |

FOREIGN PATENT DOCUMENTS

| | | | | | |
|---|---|---|---|---|---|
| CN | 209107359 U | * | 7/2019 | | |
| CN | 110418232 A | * | 11/2019 | ........... | H04R 1/1041 |
| WO | WO-2014061578 A1 | * | 4/2014 | ........... | H04R 1/1041 |

* cited by examiner

*Primary Examiner* — David L Ton
(74) *Attorney, Agent, or Firm* — Chang & Hale, LLP (57) ABSTRACT

A system and method for automatically and dynamically controlling the output (e.g., volume) of an audio headphone device is disclosed, which includes detecting the invocation of the acoustic reflex with an audio headphone device. The disclosed system can measure the response of the tympanic membrane and middle ear to various SPL and frequencies. That information may be used for automated or customized warning or limiting levels either within the headphone, or at the audio playback device.

21 Claims, 5 Drawing Sheets

```
┌─────────────────────────────────────────────────────────────────┐
│ GENERATE A FIRST AUDIO SIGNAL BASED ON A RECEIVED AUDIO PROGRAM │
│ HAVING A FIRST ADJUSTABLE AMPLITUDE AND A SECOND AUDIO TEST     │
│ SIGNAL HAVING AN ADJUSTABLE FREQUENCY AND A SECOND ADJUSTABLE   │
│ AMPLITUDE AT A PROCESSOR WITHIN AN AUDIO HEADPHONE DEVICE       │
│                              502                                │
└─────────────────────────────────────────────────────────────────┘
                                 │
                                 ▼
┌─────────────────────────────────────────────────────────────────┐
│ PROPAGATE THE FIRST AUDIO SIGNAL AND THE SECOND AUDIO TEST      │
│ SIGNAL FROM A SPEAKER OR A TRANSDUCER OF THE AUDIO HEADPHONE    │
│ DEVICE AT AN ADJUSTABLE SOUND PRESSURE LEVEL (SPL) BASED ON THE │
│ FIRST ADJUSTABLE AMPLITUDE AND THE SECOND ADJUSTABLE AMPLITUDE  │
│ AT A DRIVER WITHIN THE AUDIO HEADPHONE DEVICE                   │
│                              504                                │
└─────────────────────────────────────────────────────────────────┘
                                 │
                                 ▼
┌─────────────────────────────────────────────────────────────────┐
│ RECEIVE A COMPOSITE AUDIO SIGNAL COMPRISING AT LEAST THE SECOND │
│ AUDIO TEST SIGNAL AND A REFLECTION OF THE SECOND AUDIO TEST     │
│ SIGNAL, AS REFLECTED FROM A TYMPANIC MEMBRANE OF A USER AT A    │
│ MICROPHONE WITHIN THE AUDIO HEADPHONE DEVICE WHEN DISPOSED      │
│ WITHIN AN EAR CANAL OF THE USER                                 │
│                              506                                │
└─────────────────────────────────────────────────────────────────┘
                                 │
                                 ▼
┌─────────────────────────────────────────────────────────────────┐
│ ISOLATE THE SECOND AUDIO TEST SIGNAL AND THE REFLECTION OF THE  │
│ SECOND AUDIO TEST SIGNAL FROM A REMAINDER OF THE COMPOSITE      │
│ SIGNAL                                                          │
│                              508                                │
└─────────────────────────────────────────────────────────────────┘
                                 │
                                 ▼
┌─────────────────────────────────────────────────────────────────┐
│ ANALYZE THE SECOND AUDIO TEST SIGNAL AND THE REFLECTION OF THE  │
│ SECOND AUDIO TEST SIGNAL TO DETERMINE WHETHER AN ACOUSTIC       │
│ REFLEX IS TRIGGERED                                             │
│                              510                                │
└─────────────────────────────────────────────────────────────────┘
                                 │
                                 ▼
┌─────────────────────────────────────────────────────────────────┐
│ ACTIVATE A PREVENTATIVE SEQUENCE UNIQUE TO THE USER WHEN THE    │
│ ANALYSIS INDICATES THAT AN ACOUSTIC REFLEX IS TRIGGERED         │
│                              512                                │
└─────────────────────────────────────────────────────────────────┘
```

FIG. 5

ACOUSTIC REFLEX DETECTION

PRIORITY CLAIM AND CROSS-REFERENCE TO RELATED APPLICATION

This application claims the benefit under 35 U.S.C. § 119(e)(1) of U.S. Provisional Application No. 63/076,493, filed Sep. 10, 2020, which is hereby incorporated by reference in its entirety.

BACKGROUND

At least 17% of Americans between 20 and 65 have some level of significant noise-induced hearing loss, and with the category-leading explosive growth of in-ear headphone offerings in recent years, this percentage is only growing. In 2019, Apple changed its AirPods from a non-sealed on-ear form factor to a semi-sealed in-ear design, further sending the earbud market into overdrive (with analyst estimates placing 2019 AirPod sales alone at ~$6 billion). Just over 234 million earbuds were sold worldwide in 2020, and earbud-specific compound annual growth rates are expected to average 20.3% through 2027.

An additional key driver of the underlying problem is the fact that in-ear monitors (IEMs) are very efficient at delivering acoustic energy to the eardrum. Of particular note is the fact that damage is cumulative, often not symptomatic until later in life, and once begun, noise-induced hearing loss is permanent. Such hearing loss has become ubiquitous among aging musicians—including Sting, Phil Collins, & Huey Lewis, among many others—who were early adopters of the technology and who used in-ear monitors during their careers. Such performers have become the proverbial canaries in the coal mine.

To further exacerbate the situation, human ears are very efficient machines. As sound pressure increases, the Acoustic Reflex kicks in in people with undamaged hearing. This ASR reaction is the built-in mechanism Mother Nature gave us to protect our hearing; it limits the movement of the eardrum to safeguard the middle ear, but in the process leads to a lower perception of sound volume. And stimulation in one ear produces a like reaction in both ears. So, what's our normal response to this reflex? Turn up the volume! Which is, of course, even worse for us in the long term.

Recent data shows that noise-related hearing loss is becoming more and more prevalent, primarily because its onset is often the result of a "slow burn." Depending on the sound levels involved, it can take ten, twenty, or more years for such damage to become noticeable—since in-ear monitor and earbuds have only gained widespread traction over the past two decades, it makes sense that many early adopters of the technology are only beginning to perceive hearing damage now.

And the problem is only gaining steam. Studies show that 46% of young people ages 11 to 19 are increasingly experiencing signs of some sort of potential hearing impediment. According to the Third National Health and Nutrition Examination Survey, published in The Journal of the American Medical Association (JAMA), as many as one in five teens are afflicted, exhibiting symptoms such as ringing, buzzing, roaring, or pain in their ears some or all the time. And that's not all. The scientists, who have been tracking adolescent hearing since 1988, have noticed a whopping 31 percent rise in hearing loss among teens in this age group.

If this goes unchecked, we're looking at some severe long-term consequences. One look at the Baby Boomer generation is all it takes to see that. Affliction rates in boomers are fast approaching the half-way mark, with roughly 44% showing signs of significant hearing loss by age 69. Audiology sales and clinics are growing at double-digit rates, and hearing loss has become one of the most common chronic conditions among adults worldwide.

While a number of so-called solutions exist for this problem, most of these focus on one of two things: First, a generalized across-the-board volume restriction based on signal levels or similar measurements; Second, noise-limiting software that uses equalization and similar techniques in an attempt to isolate voices or reduce background and other ambient noise.

In both cases, the Sound Pressure Levels (SPLs) produced by typical headphones are used to create the benchmarks. And in both cases the signal levels used are almost entirely arbitrary, since they fail to account for both the efficiency of the earbuds—which can vary widely depending on quality and numerous other factors—and certain traits unique to a particular user, such as age, physiology, and any existing hearing difficulties.

It bears mentioning that most devices today (including smartphones, digital music players, True Wireless earbuds, etc.) can produce signal levels high enough to easily cause permanent hearing damage, especially if there are pre-existing conditions that may be exacerbated by high Sound Pressure Level (SPL), and such devices only warn users when one of the preset signal levels is reached, if they are capable of providing any warning at all. Of course, in most cases the user can simply ignore the warning and increase the volume, anyway.

SUMMARY

Implementations herein disclose techniques, devices, and systems for automatically and dynamically controlling the output (e.g., volume) of an audio headphone device, and include detecting the invocation of the acoustic reflex with an earbud (e.g., IEM) or other headphone, as well as detecting other hearing maladies, such as middle ear otitis media, retro-cochlear lesion, tonic tensor tympani syndrome, or other ear dysfunction.

The disclosed techniques, devices, and systems can measure the response of the tympanic membrane and middle ear to various sound pressure levels (SPL) and frequencies. That information may be used for automated or customized warning or to limit levels either within the earbud or headphone, or at the audio playback device.

In various implementations, an apparatus is disclosed comprising an audio headphone device (such as a wireless in-ear monitor (IEM)), which includes a processor configured to generate a first audio signal based on a received audio program (e.g., a music recording) that has a first adjustable amplitude, and also to generate a second audio test signal that has an adjustable frequency and a second adjustable amplitude. The audio headphone device also has a driver configured to propagate the first audio signal and the second audio test signal from a speaker or a transducer of the audio headphone device at an adjustable sound pressure level (SPL) based on the first adjustable amplitude and the second adjustable amplitude.

The audio headphone device includes an in-ear microphone configured to receive a composite audio signal comprising at least the second audio test signal and a reflection of the second audio test signal, as reflected from a tympanic membrane (e.g., eardrum) of a user. The processor is configured to isolate the second audio test signal and the reflection of the second audio test signal from the remainder of the composite signal, analyze the second audio test signal and the reflection of the second audio test signal, and activate a preventative sequence unique to the user when the analysis indicates an acoustic reflex is triggered. In an embodiment, the preventative sequence includes setting an upper sound pressure level (SPL) limit for the audio headphone device, unique to the user, based on results of the analysis. In another embodiment, the processor is configured to analyze the second audio test signal and the reflection of the second audio test signal to determine whether an acoustic reflex has been triggered, and to dynamically set an upper limit on the SPL or on the first adjustable amplitude to a value less than that which triggers an acoustic reflex of the user. In an example, the processor is configured to dynamically control the volume based on generating a plurality of second audio test signals and analyzing the plurality of second audio test signal and associated reflections of the second audio test signals. Further, the audio headphone device can have an on-board memory, configured to store analysis data, including acoustic reflex threshold (ART) data for a plurality of users.

In an implementation, the audio headphone device includes a communications transceiver configured to wirelessly receive the audio program from an audio source and also to wirelessly send a warning to the audio source when the acoustic reflex is triggered and/or to wirelessly transmit acoustic reflex data to the audio source.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

For this discussion, the devices and systems illustrated in the figures are shown as having a multiplicity of components. Various implementations of devices and/or systems, as described herein, may include fewer components and remain within the scope of the disclosure. Alternately, other implementations of devices and/or systems may include alternate or additional components, or various combinations of the described components, and remain within the scope of the disclosure. Shapes and/or dimensions shown in the illustrations of the figures are for example, and other shapes and or dimensions may be used and remain within the scope of the disclosure, unless specified otherwise.

DETAILED DESCRIPTION

Overview

Figure 1:
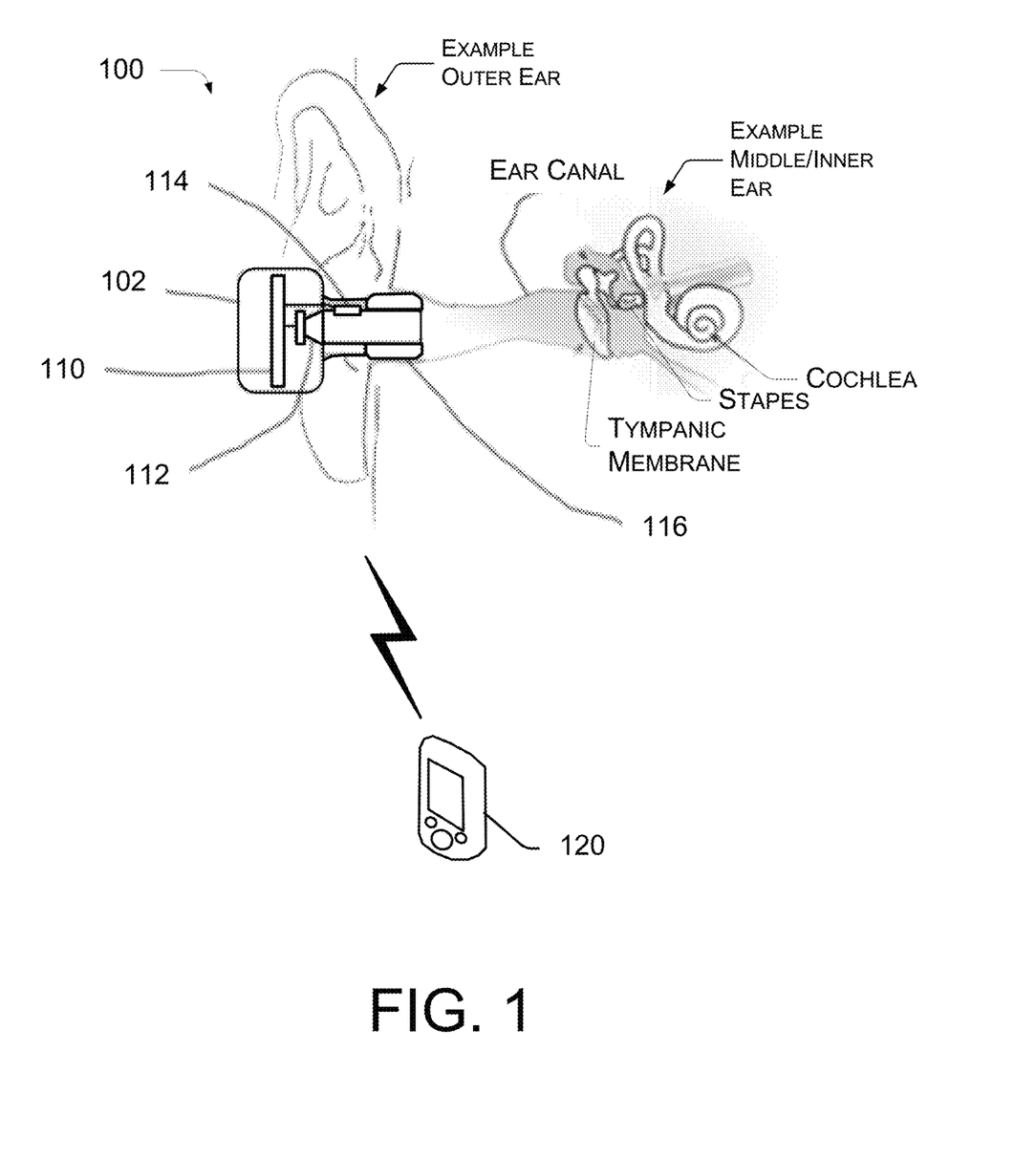
FIG. 1 is a diagram showing an example dynamic sound pressure limiting (DSPL) system in an example application, according to an embodiment.

Playback of audio through earbuds or headphones may produce sound pressures that can damage the user's hearing, especially if there are pre-existing conditions that may be exacerbated by a high Sound Pressure Level (SPL). The disclosed acoustic reflex detection system or Dynamic Sound Pressure Limiting ("DSPL") System 100 claimed herein solves this problem.

By measuring the condition of the tympanic membrane and middle ear, the DSPL system 100 can limit the magnitude of the sound pressures produced and/or warn the user of the possibility that damage may occur. Sound pressure level measurement can occur under typical sound pressure levels or at increased levels.

The disclosed techniques, devices, and systems differ from what currently exists. Currently, audio source devices (e.g., phone, mp3 player, etc.) that create audio programs for earbuds or headphones may have a preset or adjustable "loudness" setting that limits the output level of the device. Other devices may include a warning that warns the user when a preset loudness level is output by the device.

These preset levels can be somewhat arbitrary and may not be personalized to the physical needs of the particular user, who may experience hearing damage at lower or higher SPL than the preset audio source device level. In order to accurately determine if the user needs to be warned at a particular SPL or to set a limit on the SPL produced by earbuds or headphones, a professional assessment (such as an audiologist) is currently required. Then, preset levels on the audio playback device or earbud/headphones would need to be customized for the user, based on the assessment, which in most cases is not possible. Instead, the user must make a best-guess as to whether their sound listening level is harmful for their unique physiology and condition.

Disclosed techniques, devices, and systems provide an example DSPL system 100 that can measure the user's physical response to SPL levels and determine the personalized level at which to warn or limit the sound pressure level output for that user. Also, in alternate embodiments, the DSPL system 100 can be incorporated into a medical device used to diagnose or treat hearing conditions. For example, the DSPL system 100 can measure the response of the tympanic membrane and middle ear to various SPL levels and sound frequencies. The measured information may be used by the DSPL system 100 for automated customization of the warning level or sound output limit levels either within an earbud or headphone, or at the audio playback device. For instance, the playback output can be automatically and dynamically limited to SPL levels that will not trigger an acoustic reflex (AR) of the middle ear.

Figure 2:
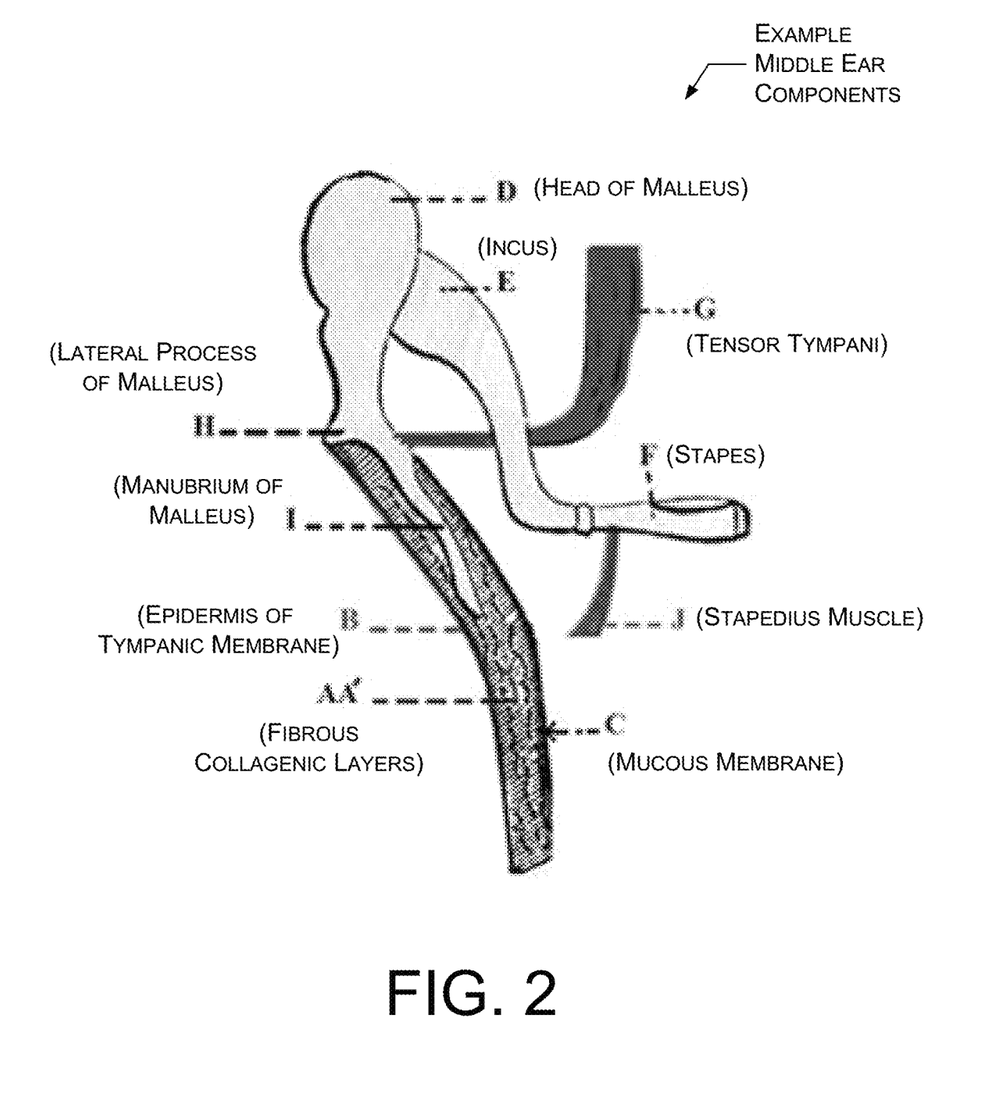
FIG. 2 is an anatomical illustration showing some of the components of the middle ear and their connections.

Referring to FIGS. 1 and 2, the acoustic reflex (AR) is a natural and involuntary protection mechanism of the middle ear. Bones of the middle ear (e.g., the stapes or "stirrup" (F) and the malleus or "hammer" (D)) are mechanically linked to the tympanic membrane or "eardrum." Tiny muscles within the middle ear are coupled to these very small bones by tendons. The stapedius muscle (J) pulls on the stapes (F) and the tensor tympani muscle (G) pulls on the malleus (D) to change the tension of the tympanic membrane. The greater the tension of the tympanic membrane, the less it is able to vibrate, and thereby to transmit sound energy to the delicate components of the inner ear. Importantly, when the stapedius muscle (J) pulls on the stapes (F), it dampens the vibrations of that bone, which also serves to limit the vibrational energy transmitted to the cochlea. The tension of the tympanic membrane is a dynamic real-time indicator of the amount of contraction of the stapedius muscle (J).

High sound pressure levels (SPLs) received by the human ear cause the stapedius muscle (J) to involuntarily contract, which is referred to as the acoustic reflex (AR) (sometimes called the stapedius reflex or tympanic reflex). The level of SPL (at a particular frequency) that triggers the AR is called the acoustic reflex threshold (ART). This involuntary contraction of the stapedius muscle (J) increases the tension of the tympanic membrane and dampens the vibrations of the stapes (F), which decreases the transmission of vibrational energy to the cochlea. Vibrational energy is converted by hair-like cells within the cochlea into electrical impulses that are perceived by the brain as sounds. It is the delicate hair-like cells within the cochlea that can die if subjected to high vibrational energy, which can result in partial or complete hearing loss at the frequencies of the damaged cells.

In many animals, the AR is the contraction of both the stapedius muscle (J) and the tensor tympani muscle (G). However, in humans, the AR consists of the contraction of the stapedius muscle (J) alone. The AR naturally works to dampen or prevent the high vibrational energy that can damage the hair-like cells from entering the cochlea, but it is unique to each person (based on age, health, genetics, history, ear damage, etc.). However, if the SPL is great enough, the high energy is transmitted into the cochlea nonetheless. Although, if the SPL is limited to less than the level (for a particular person) that will activate the AR for that person (i.e., less than the person's ART), their hearing can be protected from high SPL levels.

EXAMPLE IMPLEMENTATIONS

Referring to FIGS. 1-4, in various implementations, the DSPL system 100 actively monitors and measures sound reflected off the eardrum of the user, while the user is using audio headphones. The DSPL system 100 can detect the activation of the user's acoustic reflex (AR), which is an indicator of the involuntary contraction of the stapedius muscle (J) to protect the user's inner ear from the damaging effects of high sound pressure levels (SPL). The DSPL system 100 can be integrated into an audio headphone device 102, such as an in-ear monitor (IEM) or other listening device that is placed in or at the ear of the user. The DSPL system 100 detects the activation of the AR by generating a test audio signal 302 and propagating the test audio signal 302 from a speaker 112 (or other transducer). The test audio signal 302 is reflected off the tympanic membrane (eardrum) of the user, and the test audio signal 302 and the reflected test audio signal 304 are captured by a microphone 114 disposed between the speaker 112 and the eardrum of the user. In an embodiment, where the audio headphone device 102 comprises an in-ear monitor (IEM), the microphone 114 can be disposed near the ear tip 116 of the IEM 102.

Figure 3:
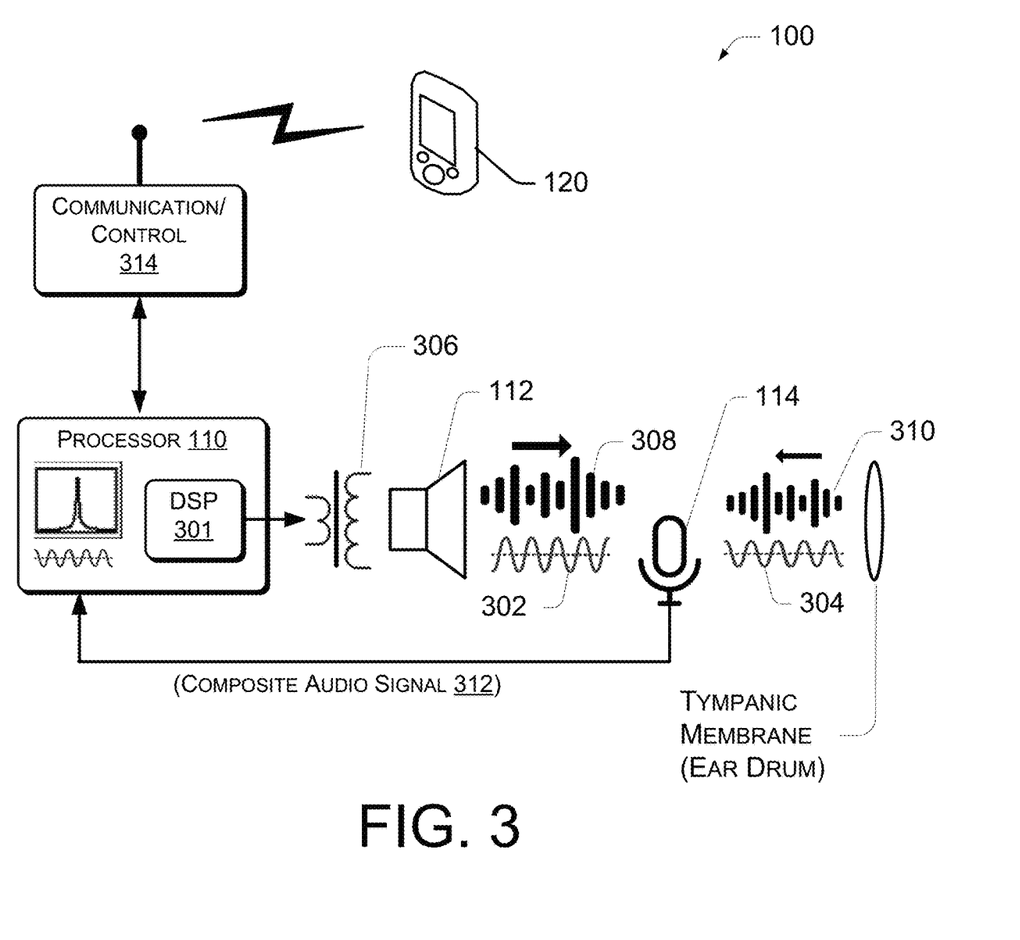
FIG. 3 is a functional diagram showing the propagation and reception of signals along with associated analysis, according to an embodiment.

An interaction of the test audio signal 302 and the reflected test audio signal 304 is analyzed at a processor 110, including determining the tension of the eardrum from the shape of the resonant frequency response profile of the interaction of the test audio signal 302 and the reflected test audio signal 304. The determination of the tension of the eardrum also determines whether the user's AR has been triggered, which can indicate an SPL that is too high for the user. The DSPL system 100 can adjust the playback volume, set an upper limit to the playback volume, send a warning message to the audio source 120, as well as many other steps in a protective sequence tailored particularly to the user.

The DSPL system 100 will now be discussed in more detail. In an implementation, an example DSPL system 100 includes an audio headphone device 102, which has a processor 110, a driver 306 (which may comprise a transformer, an amplifier, or the like), a speaker 112 (or other transducer), and a microphone 114. In various embodiments, the DSPL system 100 may include alternate components that perform similar functions, or additional components. In one alternate embodiment, the speaker 112 and the microphone 114 are a combined component, and may use the same elements to function.

The audio headphone device 102 may comprise a wired or wireless audio listening device configured to receive an electronic audio signal in the form of an audio program (such as a music recording, for example) and to convert the signal into sound for listening by a user. The volume of the sound produced from the audio signal may be adjustable at the audio headphone device 102 or at the audio source 120. Various embodiments of an audio headphone device 102 may include in-ear monitors (IEMs), on-ear headphones, around-the-ear headphones, over-the-ear headphones, and so forth. The headphone device 102 may not be sealed, or it may be partially or fully sealed with the user's ear.

Figure 4:
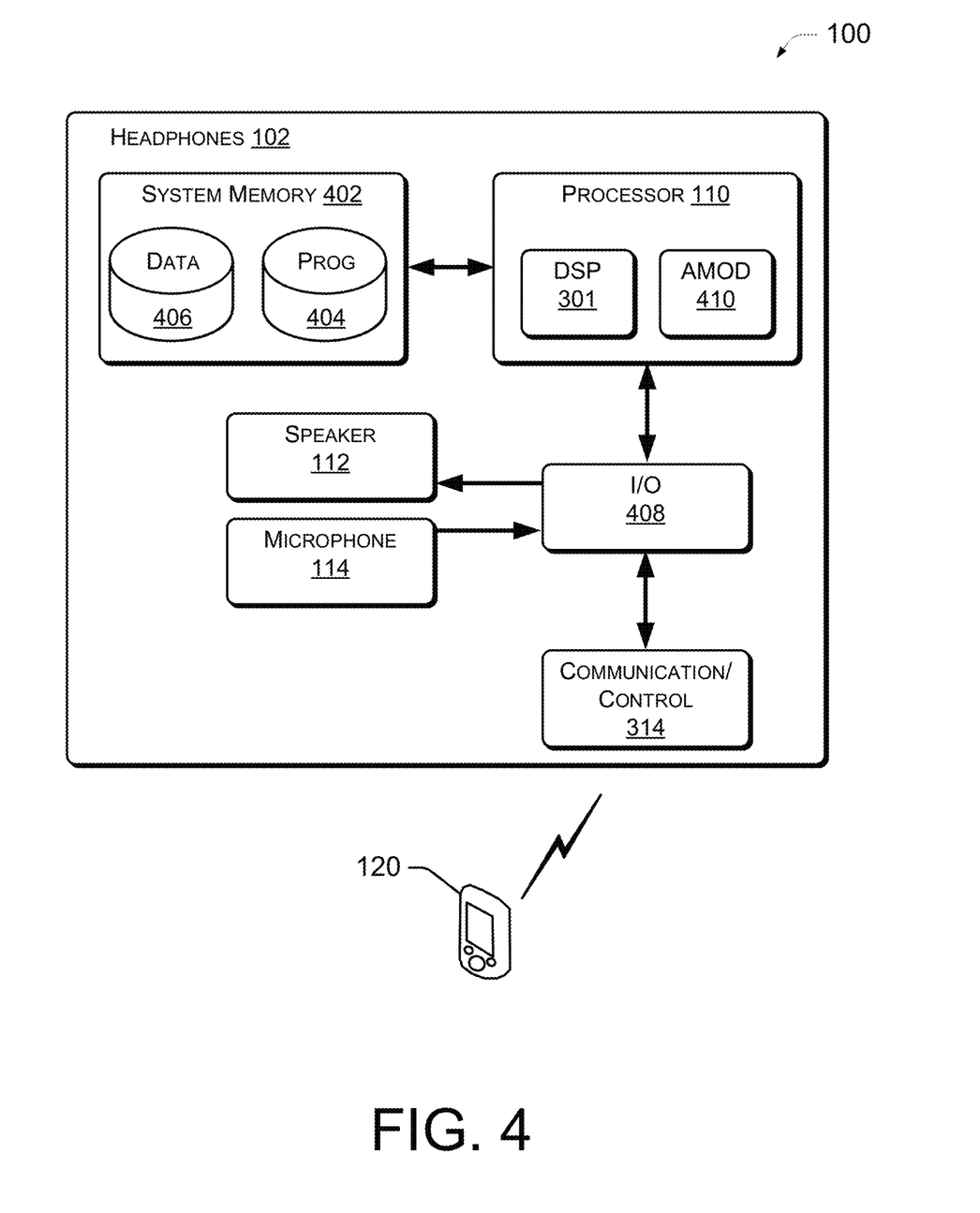
FIG. 4 is a block diagram of an example dynamic sound pressure limiting (DSPL) system, according to an embodiment.

The processor 110 may be a microprocessor or any other programmable logic device or devices that operates to perform functions based on instructions that can be stored in on-board or in separate but connected memory storage components 402. The instructions or programming 404 may be in the form of software, firmware, or other resident or remote code. In one example, the processor 110 may comprise an existing processor of an audio headphone device 102 that may be configured to provide additional functionality. In other examples, the processor 110 can be one or more added logic components to the audio headphone device 102, which may be encased within an enclosure of the audio headphones 102.

The processor 110 includes a digital signal processing (DSP) module 301 configured to generate the first audio signal 308 based on a received audio program, and also a second audio test signal 302. However, the first audio signal 308 and the audio program are optional. The processor 110 may generate the first 308 and second 302 audio signals at separate moments in time or concurrently. In an example, the processor 110 may generate the test signal 302 at breaks between segments of the first signal 308 (e.g., between songs, etc.). Alternately, the processor 110 may generate the test signal 302 during the propagation of the first signal 308. Also, the processor 110 may generate the test signal 302 prior to beginning the audio program, as a calibration or baseline reading of the user's eardrum. This baseline reading can be stored and used to compare with subsequent test results during playback of the audio program. The first 308 and second 302 audio signals are received from the DSP 301 by the driver 306, which propagates the signals via the speaker 112 (or transducer) into the user's ear canal at an adjustable sound pressure level (DPL) based on a user-adjustable amplitude. Multiple speakers 112 (and drivers 306) may also be used.

The test signal 302 can be generated at various frequencies and amplitudes (SPL) for detecting the user's AR. For instance, the processor 110 can iteratively adjust the amplitude and/or the frequency of the second audio test signal 302 to find and detect the acoustic reflex threshold (ART) of the user. The test signal 302 may be a short duration "white noise" chirp, or the like, which may be audible or inaudible to the user.

The test signal 302 is propagated into the ear canal of the user and is reflected off the tympanic membrane of the user. The interaction of the test signal 302 and the reflected test signal 304 may have a resonant frequency, which may be partly based on the length of the user's ear canal, and is determined by the tension of the tympanic membrane. The tension of the tympanic membrane can result in a resonant frequency of between 500 Hz and 2000 Hz, but it may fall outside that range. The test signal 302 can also be adjusted in frequency and/or amplitude for audio headphone devices that do not fit within the user's ear, resulting in an adjustment to the analysis of the reflected test signal 304 as well.

The processor 110 includes an analysis module 410 that receives the test signal 302 and the reflected test signal 304 from the microphone 114 and processes them (e.g., including an interaction comprising a resonance cancellation or amplification between the two signals) to determine the tension of the tympanic membrane. (Multiple microphones 114 may be used to improve accuracy.) For instance, the processor 110 may use a Fourier analysis technique (or similar) to convert the test signal 302, the reflected test signal 304, and/or the interaction of the test signal 302 and the reflected test signal 304 from a time-domain signal to a frequency-domain signal, resulting in a frequency response profile (e.g., ¼ wave resonance) that resembles a spike at the resonant frequency. In an embodiment, the tighter the tympanic membrane is, the sharper the resulting frequency response profile spike will be. For instance, a sharper narrow spike profile is indicative of a "hard" reflection off the eardrum, meaning a tighter eardrum (e.g., a contraction of the stapedius muscle), while a softer, more rounded and broader spike profile is indicative of a "softer" reflection off the eardrum, meaning a more relaxed eardrum (e.g., a relaxed stapedius muscle). The processor 110 can be programmed to measure the shape (e.g., sharpness of spike profile, width of spike, etc.) of the frequency response profile to detect whether the user's AR has been triggered.

Since the microphone 114 is situated between the speaker 112 and the eardrum, the microphone 114 receives any outgoing audio signals from the speaker 112 as well as any reflected audio signals from the eardrum. For example, the first audio signal 308 reflects off the eardrum to form a reflected first audio signal 310 and the second audio test signal 302 reflects off the eardrum to form a reflected second audio test signal 304. The microphone 114 receives a composite audio signal 312 that may include some or all of these signals, including the test signal 302 and the reflected second audio test signal 304.

The analysis module 410 of the processor 110 is configured to isolate the second audio test signal 302 and the reflected second audio test signal 304 from the remainder of the composite audio signal 312 (if any) received at the microphone 114. The processor 110 may use a similar cancellation method (e.g., inverted signals) as that used for noise cancellation processing to isolate the second audio test signal 302 and the reflected second audio test signal 304. Alternately, the processor 110 may use digital filtering or other techniques to perform the isolation.

The results of the analysis of the second audio test signal 302 and the reflection of the second audio test signal 304 may be stored as data 406 in the memory 402. Multiple results may be analyzed by the processor 110 to determine the user's ART, whether the user's AR has been triggered, or to detect a hearing malady. For instance, the processor 110 can be programmed to detect hearing maladies that are indicated by various results or patterns of results. For multiple users that may use the DSPL system 100, the unique analysis data and results for each user (including each user's ART data) may be temporarily or permanently stored in the memory 402.

When the results of an analysis indicate that the user's AR has been triggered, the processor 110 can activate a preventative sequence unique to the user. For instance, the DSPL system 100 can include a communication/control module 314, comprising a transceiver and control components, which may be a separate system communicatively coupled to the processor 110 or may be integral to the processor 110. In an embodiment, the communication/control module 314 can be configured to receive the audio program from the audio source 120 (either by wire or wirelessly). Further, the communication/control module 314 can communicate with the analysis module 410 or the processor 110 (through an input/output module 408 in some cases) and can be configured to send a warning to the audio source 120 when the user's acoustic reflex is triggered. This can allow the user to adjust the SPL (e.g., volume) of the audio headphones 102 according to the user's needs.

The communication/control module 314 can also dynamically set an upper limit on the SPL or on the amplitude of the audio playback (at the DSP 301 or the driver 306, for example) to a value less than that which triggers the acoustic reflex of the user. The communication/control module 314 can also automatically and dynamically control the volume of the audio headphones 102 based on generating a plurality of second audio test signals 302 and analyzing the plurality of second audio test signals 302 and the associated reflections of the second audio test signals 304.

In an implementation involving multiple users, the processor 110 is configured to provide unique protection levels for individual users. For instance, the processor 110 can be configured to set a first upper sound pressure level (SPL) limit for the audio headphone device 102 for a first user, based on first results of analyzing the second audio test signal 302 and the reflection of the second audio test signal 304, and can set a second, different upper sound pressure level (SPL) limit for the audio headphone device 102 for a second user, based on second results of analyzing the second audio test signal 302 and the reflection of the second audio test signal 304, while the DSPL system 100 is being used by the second user. The first and second results may or may not be stored in memory 402.

Example Process

Figure 5:
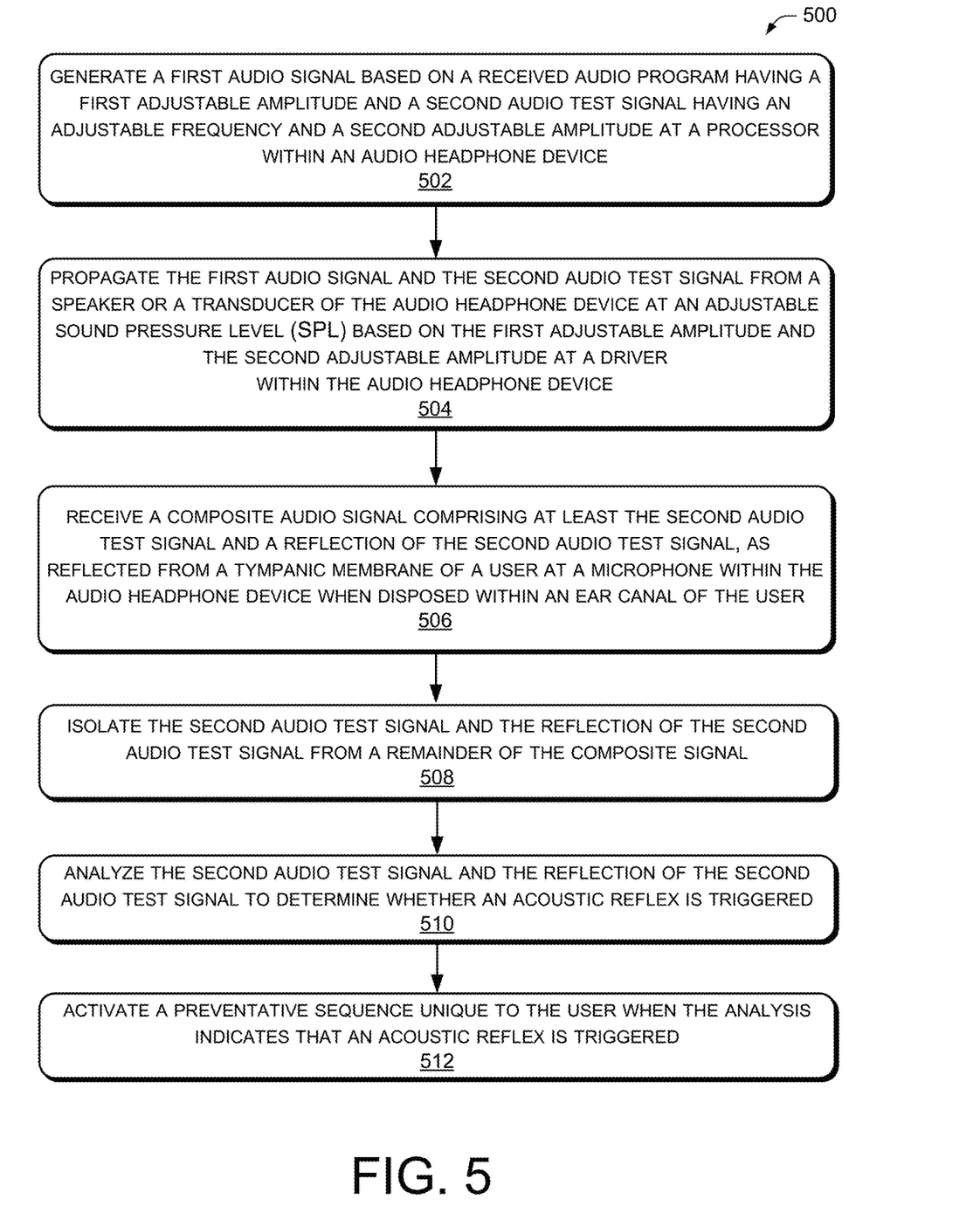
FIG. 5 shows an example flow chart for a process of controlling an output of an audio headphone device, according to an embodiment.

FIG. 5 is a flow diagram illustrating an example processes 500 for controlling an output of an audio headphone device (as in the audio headphone device 102, discussed above), according to various embodiments. The process 500 described is an example that is not intended to be limiting. Further, the process 500 is described with respect to FIGS. 1-4, and may also describe a corresponding apparatus, structure, system, or the like. For example, one embodiment of a system 100 for controlling an output of an audio headphone device is shown at FIG. 1.

The order in which the process 500 is shown and described is not intended to be construed as a limitation, and any number of the described process steps can be combined in any order to implement the process 500, or alternate processes. Additionally, individual steps may be added or deleted from the process 500 without departing from the spirit and scope of the subject matter described herein. Furthermore, the process 500 can be implemented in any suitable materials, or combinations thereof, including hardware, firmware, software, etc. without departing from the scope of the subject matter described herein. In alternate implementations, other techniques may be included in the process 500 in various combinations, and remain within the scope of the disclosure.

At block 502, the process includes generating a first audio signal based on a received audio program having a first adjustable amplitude and a second audio test signal having an adjustable frequency and a second adjustable amplitude at a processor within an audio headphone device.

In an implementation, the process includes generating and propagating the second audio test signal and isolating and analyzing the second audio test signal and the reflection of the second audio test signal prior to propagating the first audio signal, and storing a baseline response to the analyzing.

At block 504, the process includes propagating the first audio signal and the second audio test signal from a speaker or a transducer of the audio headphone device at an adjustable sound pressure level (SPL) based on the first adjustable amplitude and the second adjustable amplitude at a driver within the audio headphone device. The first audio signal and the second audio test signal may be propagated concurrently or separately. In an embodiment, the process includes propagating the second audio test signal at a plurality of predetermined intervals during playback of the received audio program.

At block 506, the process includes receiving a composite audio signal comprising at least the second audio test signal and a reflection of the second audio test signal, as reflected from a tympanic membrane of a user at a microphone within the audio headphone device when disposed within an ear canal of the user. At block 508, the process includes isolating the second audio test signal and the reflection of the second audio test signal from a remainder of the composite signal.

In an embodiment, the process includes converting the second audio test signal and the reflection of the second audio test signal to a frequency domain representation and measuring a frequency response profile of the interaction of the second audio test signal and the reflection of the second audio test signal at the processor.

At block 510, the process includes analyzing the second audio test signal and the reflection of the second audio test signal to determine whether an acoustic reflex is triggered. In an embodiment, the process includes storing analysis data including acoustic reflex threshold (ART) data for a plurality of users at a memory storage within the audio headphone device.

At block 512, the process includes activating a preventative sequence unique to the user when the analysis indicates that an acoustic reflex is triggered. In an embodiment, the preventative sequence includes setting an upper sound pressure level (SPL) limit or an upper volume limit for the audio headphone device, unique to the user, based on the analyzing. In another embodiment, the preventative sequence includes decreasing a sound pressure level (SPL) of the audio headphone device to a level below an acoustic reflex threshold of the user. In one example, the process includes communicating a warning to a source of the audio program when the acoustic reflex is triggered.

In various implementations, additional or alternative components, techniques, sequences, or processes may be used to implement the techniques described herein. The components and/or techniques may be arranged and/or combined in various combinations, while resulting in similar or approximately identical results. It is to be understood that the techniques described may be implemented in a stand-alone manner or as part of a larger system (e.g., integrated with other systems, techniques, protocols, etc.).

CONCLUSION

While various discreet embodiments have been described throughout, the individual features of the various embodiments may be combined to form other embodiments not specifically described. The embodiments formed by combining the features of described embodiments are also within the scope of the disclosure.

What is claimed is:

1. An apparatus, comprising:
an audio headphone device, including:
a processor configured to generate a first audio signal based on a received audio program and having a first adjustable amplitude and to generate a second audio test signal having an adjustable frequency and a second adjustable amplitude;
a driver configured to propagate the first audio signal and the second audio test signal from a speaker or a transducer of the audio headphone device at an adjustable sound pressure level (SPL) based on the first adjustable amplitude and the second adjustable amplitude; and
an in-ear microphone configured to receive a composite audio signal comprising at least the second audio test signal and a reflection of the second audio test signal, as reflected from a tympanic membrane of a user,
wherein the processor is configured to isolate the second audio test signal and the reflection of the second audio test signal from a remainder of the composite signal, analyze the second audio test signal and the reflection of the second audio test signal, and to activate a preventative sequence unique to the user when the analysis indicates an acoustic reflex is triggered.

2. The apparatus of claim 1, further comprising a communications transceiver configured to wirelessly receive the audio program from an audio source and to wirelessly send a warning to the audio source when the acoustic reflex is triggered.

3. The apparatus of claim 1, further comprising a memory configured to store analysis data, including acoustic reflex threshold (ART) data for a plurality of users.

4. The apparatus of claim 1, wherein the processor is configured to iteratively adjust the second adjustable amplitude or the adjustable frequency of the second audio test signal to detect an acoustic reflex threshold (ART) of the user.

5. The apparatus of claim 1, wherein the preventative sequence includes setting an upper sound pressure level (SPL) limit for the audio headphone device, unique to the user, based on results of the analysis.

6. The apparatus of claim 1, wherein the audio headphone device comprises a wireless in-ear monitor (IEM).

7. The apparatus of claim 1, wherein the processor is configured to generate the first audio signal and the second audio test signal at separate moments in time or concurrently.

8. An apparatus, comprising:
a wireless in-ear monitor (IEM), including:
a processor configured to generate a first audio signal having a first adjustable amplitude, based on a wirelessly received audio program from a remote audio source and to generate a second audio test signal having an adjustable frequency and a second adjustable amplitude;
a driver configured to propagate the first audio signal and the second audio test signal from a speaker or a transducer of the IEM at an adjustable sound pressure level (SPL) based on the first adjustable amplitude and the second adjustable amplitude; and
an in-ear microphone configured to receive a composite audio signal comprising at least the second audio test signal and a reflection of the second audio test signal, as reflected from a tympanic membrane of a user, wherein the processor is configured to isolate the second audio test signal and the reflection of the second audio test signal from a remainder of the composite signal, analyze the second audio test signal and the reflection of the second audio test signal to determine whether an acoustic reflex has been triggered, and to dynamically set an upper limit on the SPL or on the first adjustable amplitude to a value less than that which triggers an acoustic reflex of the user.

9. The apparatus of claim 8, further comprising a wireless communications transceiver configured to wirelessly receive the audio program from an audio source and to wirelessly transmit acoustic reflex data to the audio source.

10. The apparatus of claim 8, wherein the microphone is arranged to be disposed between the speaker or transducer of the IEM and the tympanic membrane of the user when the IEM is inserted into an ear of the user.

11. The apparatus of claim 8, wherein the processor is configured to dynamically control the volume of the IEM based on generating a plurality of second audio test signals and analyzing the plurality of second audio test signals and a plurality of associated reflections of the second audio test signals.

12. The apparatus of claim 8, wherein the processor is configured to set a first upper sound pressure level (SPL) limit for the audio headphone device for a first user, based on first results of analyzing the second audio test signal and the reflection of the second audio test signal, and to set a second, different upper sound pressure level (SPL) limit for the audio headphone device for a second user, based on second results of analyzing the second audio test signal and the reflection of the second audio test signal.

13. The apparatus of claim 8, wherein the processor is configured to generate the second audio test signal at predetermined intervals during propagation of the first audio signal.

14. A method for controlling an output of an audio headphone device, comprising:
generating a first audio signal based on a received audio program having a first adjustable amplitude and a second audio test signal having an adjustable frequency and a second adjustable amplitude at a processor within an audio headphone device;
propagating the first audio signal and the second audio test signal from a speaker or a transducer of the audio headphone device at an adjustable sound pressure level (SPL) based on the first adjustable amplitude and the second adjustable amplitude at a driver within the audio headphone device;
receiving a composite audio signal comprising at least the second audio test signal and a reflection of the second audio test signal, as reflected from a tympanic membrane of a user at a microphone within the audio headphone device when disposed within an ear canal of the user;
isolating the second audio test signal and the reflection of the second audio test signal from a remainder of the composite signal;
analyzing the second audio test signal and the reflection of the second audio test signal to determine whether an acoustic reflex is triggered; and
activating a preventative sequence unique to the user when the analysis indicates that an acoustic reflex is triggered.

15. The method of claim 14, further comprising generating and propagating the second audio test signal and isolating and analyzing the second audio test signal and the reflection of the second audio test signal prior to propagating the first audio signal, and storing a baseline response to the analyzing.

16. The method of claim 14, further comprising propagating the second audio test signal at a plurality of predetermined intervals during playback of the received audio program.

17. The method of claim 14, further comprising converting the second audio test signal and the reflection of the second audio test signal to a frequency domain representation and measuring a frequency response profile of the interaction of the second audio test signal and the reflection of the second audio test signal at the processor.

18. The method of claim 14, further comprising storing analysis data including acoustic reflex threshold (ART) data for a plurality of users at a memory storage within the audio headphone device.

19. The method of claim 14, further comprising communicating a warning to a source of the audio program when the acoustic reflex is triggered.

20. The method of claim 14, wherein the preventative sequence includes setting an upper sound pressure level (SPL) limit or an upper volume limit for the audio headphone device, unique to the user, based on the analyzing.

21. The method of claim 14, wherein the preventative sequence includes decreasing a sound pressure level (SPL) of the audio headphone device to a level below an acoustic reflex threshold of the user.

* * * * *